United States Patent
Dershem et al.

(10) Patent No.: US 6,429,281 B1
(45) Date of Patent: Aug. 6, 2002

(54) HYDROPHOBIC, HIGH TG CYCLOALIPHATIC EPOXY RESINS

(75) Inventors: Stephen M. Dershem, San Diego; Frank G. Mizori, La Mesa, both of CA (US)

(73) Assignee: Loctite, Rocky Hill, CT (US)

( * ) Notice: Subject to any disclaimer, the term of this patent is extended or adjusted under 35 U.S.C. 154(b) by 0 days.

(21) Appl. No.: 09/347,091

(22) Filed: Jul. 1, 1999

(51) Int. Cl.[7] ................ C08L 63/00; C07D 303/06
(52) U.S. Cl. .............. 528/412; 528/26; 528/40; 528/297; 528/410; 528/418; 528/421; 525/474; 525/523; 525/533; 549/543; 549/544; 549/545; 549/546; 549/547
(58) Field of Search ............... 549/543, 544, 549/545, 546, 547; 525/533, 523; 528/410, 412, 418, 421, 297

(56) References Cited

U.S. PATENT DOCUMENTS

| | | | | |
|---|---|---|---|---|
| 2,927,934 A | * | 3/1960 | Greenspan | |
| 3,183,249 A | * | 5/1965 | Wiese | |
| 3,646,113 A | | 2/1972 | Rick et al. | ............... 260/486 R |
| 4,079,091 A | | 3/1978 | Matsuno | ............... 260/666 PY |
| 4,381,396 A | | 4/1983 | Ryang | ............... 549/237 |
| 4,789,727 A | * | 12/1988 | Sun | |
| 4,855,467 A | * | 8/1989 | Colborn | |
| 4,923,942 A | * | 5/1990 | Takeyama | |
| 5,466,838 A | * | 11/1995 | Murahashi | |
| 5,783,639 A | | 7/1998 | Kataoka et al. | ............. 525/286 |

FOREIGN PATENT DOCUMENTS

| | | | |
|---|---|---|---|
| EP | 453275 | * | 10/1991 |
| EP | 0531175 A2 | | 9/1992 |
| GB | 933791 | * | 8/1963 |
| JP | 126658 | * | 12/1974 |

OTHER PUBLICATIONS

Chemical Abstract 115:244048 of DD286437 1/91.*
International Search Report in PCT Application No. PCT/US00/18405 dated Sep. 22, 2000.
Lecamp L., "Photocurable polydimethyl siloxane by cationic methods," European Polymer Journal vol. 33, No. 9, pp. 1453–1462.

* cited by examiner

Primary Examiner—David J. Buttner
(74) Attorney, Agent, or Firm—Stephen E. Reiter; Kevin J. Forrestal; Foley & Lardner

(57) ABSTRACT

In accordance with the present invention there are provided cycloaliphatic epoxy compounds and thermosetting resin compositions prepared therefrom. Inventive compounds are based on polycyclic hydrocarbon backbones, as illustrated by the following exemplary structure:

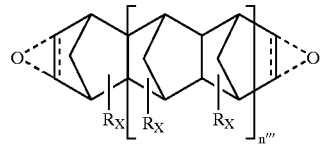

(XII)

wherein:
  each R is independently lower alkyl or halogen,
  n''' is 1 up to about 8, and
  each x is independently 0, 1, or 2.

Inventive compounds provide resins with desirable characteristics such as, for example, hydrophobicity, high Tg values, ionic purity, hydrolytic stability, and the like.

13 Claims, 1 Drawing Sheet

HYDROPHOBIC, HIGH TG CYCLOALIPHATIC EPOXY RESINS

FIELD OF THE INVENTION

The present invention relates to epoxy resins and their use in electronics packaging applications. In a particular aspect, the invention relates to hydrophobic epoxy resins. In another aspect, the present invention relates to high Tg resins.

BACKGROUND OF THE INVENTION

Epoxy based resins have a variety of applications in adhesives, potting compounds, laminates, composites, coatings, etc. Epoxy compounds with more than one epoxy functional group per molecule can readily be polymerized via a ring-opening, step-growth, addition mechanism to yield thermoset compositions. Epoxy resins can be homopolymerized in the presence of a suitable catalyst or via the further addition of a curing agent (e.g., amines, mercaptans, phenols, anhydrides, and the like). These cure mechanisms, in either case, do not result in the release of any volatiles, which is critical for void-free cure. Furthermore, epoxy resin thermosets are noted for their low cure shrinkage, corrosion resistance, and good electrical properties. Epoxy thermosets can also be formulated to yield tough, adherent compositions.

Epoxy resin types include glycidyl ether, aliphatic and cycloaliphatic oxirane compounds. Cycloaliphatic epoxy thermosets, in particular, are noted for their high glass transition (Tg) temperatures. High Tg thermosets are desirable since they can be used in more demanding (e.g., high temperature) applications without a significant loss of physical properties. For examples of cycloaliphatic epoxy thermosets, reference is made to Kataoka, et al. (U.S. Pat. No. 5,783,639, hereinafter "the '639 patent"). Cycloaliphatic epoxy resins have a further advantage over most glycidyl ether type resins in that they are virtually free of ionic chloride residues. Residual chloride ion contamination, by virtue of its tendency to promote corrosion of metal traces, cannot be tolerated in electronic applications at levels much greater than about ten parts per million. The glycidyl ether type epoxy resins routinely have several times this level of extractable chloride ion, and often require the use of intensive clean-up efforts to achieve acceptable levels. The cycloaliphatic resins are further distinguished over the aliphatic epoxies by their higher reactivity and ability to yield high Tg thermosets. Despite their high Tg, ionic purity, and reactivity advantages, presently commercially available cycloaliphatic epoxy resins do not yield hydrophobic thermosets. Hydrophobicity results in a low moisture content, which is desirable because moisture can cause popcorning (i.e., violent release of volatiles). Furthermore, presently commercially available cycloaliphatic epoxy resins are also noted for their susceptibility to hydrolysis in the presence of hot and humid environments. This hydrolysis problem can lead to catastrophic adhesive failure in the presence of moisture.

Accordingly, there is still a need in the art for epoxy resins that have the advantages imparted by cycloaliphatic epoxies yet which are hydrophobic in nature and have reduced susceptibility to hydrolysis.

BRIEF DESCRIPTION OF THE INVENTION

The present invention provides novel epoxy compounds which, when employed in resins, overcome the problems of hydrophilicity and hydrolytic instability associated with commercially available cycloaliphatic epoxies while maintaining the advantages of high Tg, ionic purity, and cure speed. Invention epoxy compounds are based on polycyclic hydrocarbon backbones. Specifically, invention epoxy compounds are derived from oligomers of cyclopentadiene and related vinyl and/or divinyl compounds capable of undergoing Diels-Alder cycloaddition.

Invention epoxy compounds may be cured to yield thermosets via the addition of suitable curing agents and catalysts. Certain cationic initiators can be used to promote efficient homopolymerization of these epoxy compounds. The latter cure method is particularly desirable where the lowest possible dielectric constant and moisture uptake is required. Another advantage of invention materials is that epoxy resins having much lower viscosity can be made using invention epoxy compounds than by employing prior art epoxy compounds. Invention compounds may be used as the sole epoxy component or they may be added to other epoxy compounds to enhance the ultimate performance characteristics. In a further aspect of the present invention, polycycloaliphatic epoxy and glycidyl ether epoxy functional groups may be combined in the same molecule. This capability can be especially useful in applications where it is desirable to have different levels of reactivity (such as for the formation of B-staged adhesives).

DETAILED DESCRIPTION OF THE INVENTION

Figure 1:
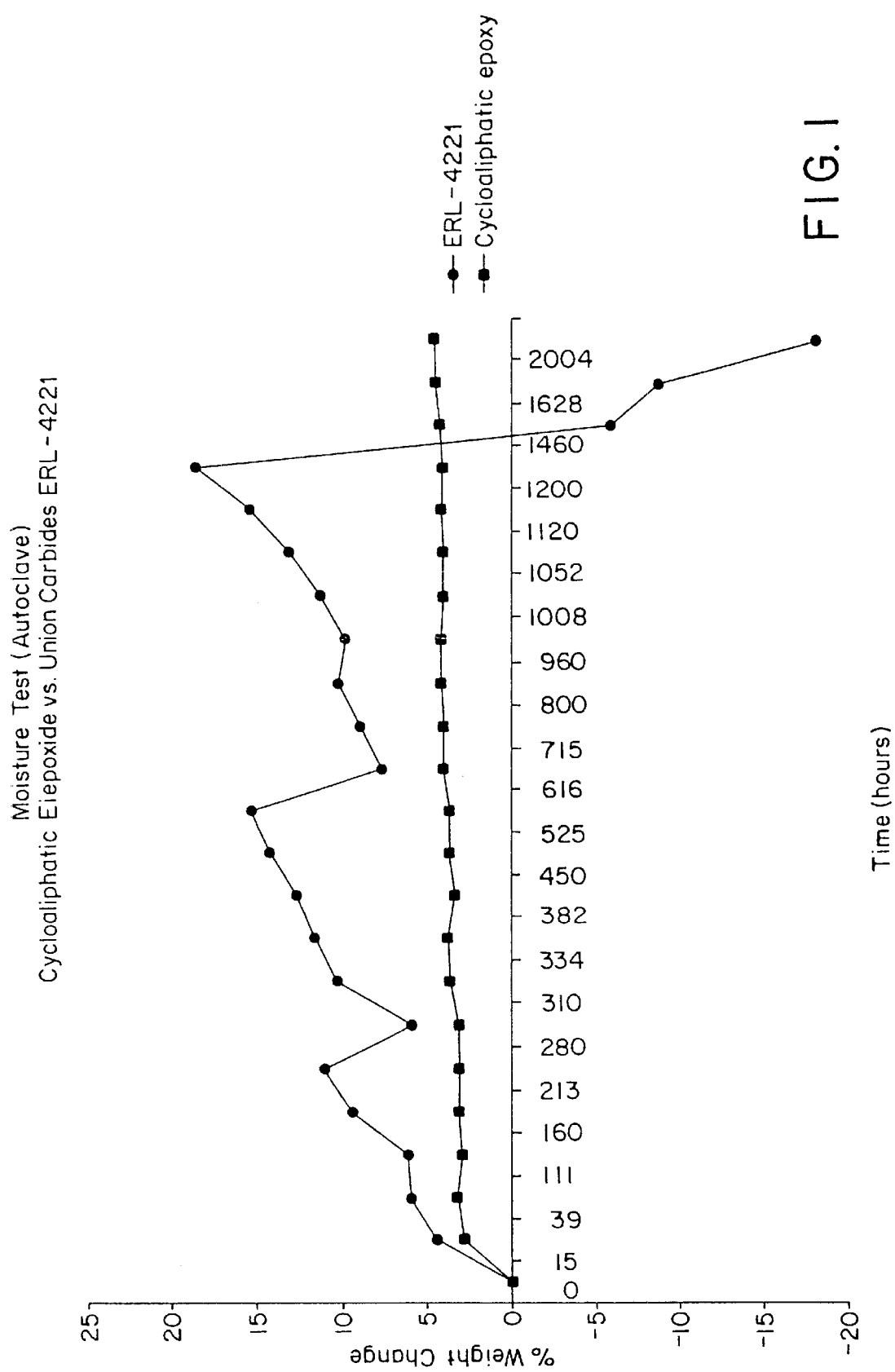
FIG. 1 graphically illustrates a comparison (average of three-runs) of an invention formulation against a commercially available resin (ERL-4221™, Union Carbide; see Example 2), and demonstrates that invention formulations are superior in both hydrophobicity (i.e., little moisture retention) and resistant to hydrolysis (i.e., little moisture uptake) whereas the prior art resin is demonstrably more hydrophilic (i.e., retains moisture) and less resistant to hydrolysis (i.e., loses substantial weight) upon exposure to heat and moisture.

In accordance with the present invention, there are provided epoxy derivatives of trimers or tetramers of optionally substituted cyclopentadiene. As will be understood by those of skill in the art, when oligomers of cyclopentadiene (CPD) are formed, they will comprise one or more bicycloheptane moieties. Other polycyclic moieties may also be present, depending on the mode of synthesis employed. Accordingly, in one aspect of the present invention, the trimers or tetramers of optionally substituted cyclopentadiene have one or more of the following structures:

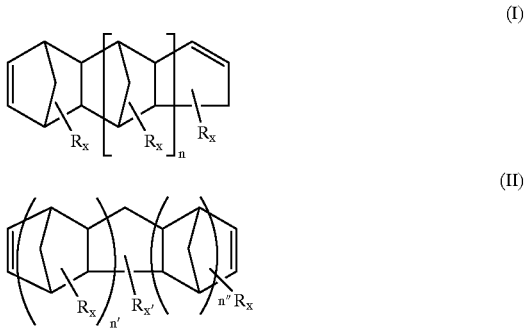

-continued (III)

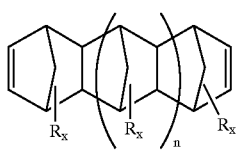

(IV)

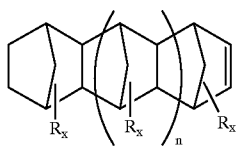

wherein:
each R is independently a lower alkyl or a halogen,
n is 1 or 2,
the sum of n'+n" is 2 or 3,
each x is independently 0, 1 or 2, and
x' is 0, 1, 2.

As will also be understood by those of skill in the art, different modes of synthesis may yield different polycyclic containing oligomers. Therefore, in accordance with another embodiment of the present invention, there are provided epoxy derivatives of optionally substituted bicycloheptenyl-containing, optionally substituted polycyclic moieties. In one aspect of the present invention, the optionally substituted bicycloheptenyl-containing, optionally substituted polycyclic moieties have one or more of the following structures:

(V)

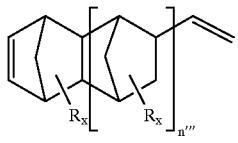

(VI)

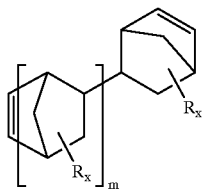

wherein:
each R is independently a lower alkyl or a halogen,
n'" is 0 up to about 8,
m is 1 up to about 9,
each x is independently 0, 1 or 2.

Polycyclic olefins as depicted in structures I–IV can be prepared by any means known to those of skill in the art, including, for example, subjecting dicyclopentadiene to Diels-Alder cycloaddition reaction conditions. Similarly, polycyclic olefins as depicted in structures V and VI can be prepared by any means known to those of skill in the art, including, for example, combining 5-vinyl-norbornene with cyclopentadiene under Diels-Alder cycloaddition reaction conditions, and the like.

In accordance with another embodiment of the present invention, there are provided bifunctional epoxy monomers having one or more of the following structures:

(VII)

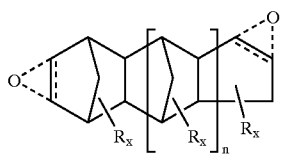

(VIII)

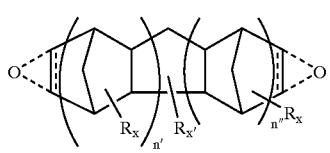

(IX)

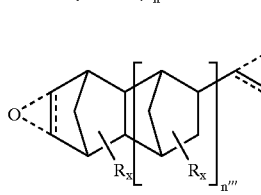

(X)

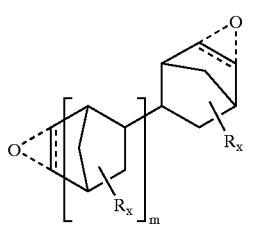

(XI)

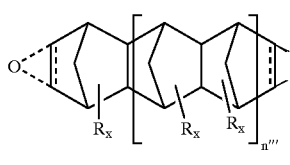

(XII)

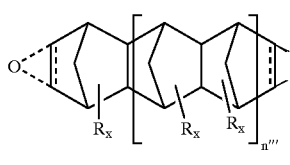

wherein:
each R is independently a lower alkyl or a halogen,
n is 1 or 2,
the sum of n'+n" is 2 or 3,
n'" is 0 up to about 8,
m is 1 up to about 9,
each x is independently 0, 1 or 2, and
x' is 0, 1, 2;
wherein at least one site of unsaturation is epoxidized.

As will be understood by those of skill in the art, the dashed lines employed in structures depicted herein signify bonds present in alternative aspects of the present invention. Thus, the dashed line inside a ring indicates an alternative structure having a double bond. The two dashed lines extending outside of a ring to an oxygen (O) atom signify an alternative structure having an epoxy moiety. Thus, when the epoxy moiety is present, there is no ring double bond at that position, and the converse is also true.

Epoxidation of compounds according to structures I through VI, in order to yield the compounds according to structures VII through XII, can be accomplished by any means known to those of skill in the art. Presently preferred methods employ the use of peracetic acid as an epoxidation agent.

It is well known to those skilled in the art that glycidyl and cycloaliphatic epoxy functional groups have dissimilar reactivity. A glycidyl ether epoxy, for example, can be homopolymerized using an imidazole catalyst while a cylcloaliphatic epoxy will not polymerize under the same conditions. In contrast, both epoxy groups can be homocured in the presence of a suitable cationic catalyst. Certain curing agents such as phenols or cyanate esters, for example, will react preferentially with the glycidyl ether functional group. Thus, mixed epoxy hybrids, such as those shown by way of example in structures XXI, and XXII below, also represent a very useful class of epoxy starting materials that can either be cured in a mode where both epoxy functional groups are reacted simultaneously, or where the two epoxy types are reacted sequentially.

(XXI)

(XXII)

Polycyclic moieties described herein can be imparted with a variety of other functional groups, both epoxy and non-epoxy, to yield bifunctional monomers. Bifunctional monomers contemplated for use according to this embodiment of the present invention have the following structure:

X—y—Z wherein:

X is a trimer or tetramer of optionally substituted cyclopentadiene bearing at least one functional group, or a radical having one of the following structures:

(XIII)

(XIV)

(XV)

(XVI)

(XVII)

(XVIII)

(XIX)

(XX)

wherein:
each R is independently a lower alkyl or a halogen,
n is 1 or 2,
the sum of n'+n" is 2 or 3,
n''' is 0 up to about 8,
m is 1 up to about 9,
each x is independently 0, 1 or 2, and
x' is 0, 1, 2;

Y is an optional bridging group,

Z is a trimer or tetramer of an optionally substituted cyclopentadiene moiety bearing at least one functional group, a radical having one of said structures (XIII), (XIV), (XV), (XVI), (XVII), (XVIII), (XIX) or (XX), an epoxy or a cycloaliphatic moiety bearing at least one functional group, wherein at least one of said functional groups on said bifunctional monomer is epoxy.

Other, non-epoxy functional groups contemplated for use in the practice of the present invention include maleimido, norbornyl, cyanate ester, (meth) acrylates, anhydrides, carboxylic acids, amines, amides, sulfides, vinyl ethers, vinyl esters, polyhydroxy hydrocarbyls, and the like.

Substituents contemplated for use on the Z moiety in the practice of the present invention are independently lower alkyl or halogen.

In one aspect of the present invention, Y is a divalent or polyvalent radical selected from:

high molecular weight straight chain or branched chain alkyl, alkylene or alkylene oxide species having from about 12 to about 500 atoms in the backbone thereof; aromatic groups having the structure:

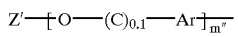

wherein:
m"=1, 2 or 3,
each Ar is a monosubstituted, disubstituted or trisubstituted aromatic or heteroaromatic ring having in the range of 3 up to 10 carbon atoms, and
Z' is a high molecular weight branched chain alkyl, alkylene or alkylene oxide species having from about 12 to about 500 atoms in the backbone thereof,
as well as mixtures thereof;
siloxanes having the structure:

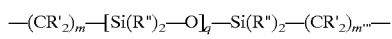

wherein:
each R' is independently, a lower alkyl or halogen,
each R" is independently selected from hydrogen, lower alkyl or aryl,
m' falls in the range of 0 up to about 10,
m''' falls in the range of 0 up to about 10, and
q falls in the range of 1 up to 50;
and the like.

When X and/or Z are radicals according to structure XX, it is presently preferred that Y is a siloxane.

Polycyclic monomers described herein are particularly well suited for use in the synthesis of thermosetting resins having a high degree of hydrophobicity and low susceptibility to hydrolysis. Therefore, in accordance with another embodiment of the present invention, there are provided thermosetting resins comprising:
(a) cycloaliphatic bifunctional epoxy monomer(s),
(b) a curing agent,
(c) optionally, a co-reactant, and
(d) optionally, a filler,
wherein said cycloaliphatic bifunctional epoxy monomer(s) have one or more of the structures VII through XII, wherein:
R, n, n'+n", n''', m, x and x' are defined as above, and
wherein at least one site of unsaturation is epoxidized.

In accordance with one aspect of the present invention, the co-reactant, if present, employed in thermosetting resins has the ability to promote ring opening of epoxides. Thus, examples of co-reactants contemplated for use in the practice of the present invention are one or more of an epoxy, a cyanate ester, an anhydride, an organic acid, a polyamine, a polyamide, a polysulfide, a polyhydroxy hydrocarbyl, and the like. It is presently preferred that a cyanate ester, a polyamine, a polyamide, a polysulfide, or a polyhydroxy hydrocarbyl be employed as co-reactants only when the bifunctional epoxy monomer is a derivative of a glycidyl ether such as those depicted in structures XX, XXI or XXII.

Cyanate ester monomers contemplated for use in the practice of the present invention contain two or more ring-forming cyanate (—O—C≡N) groups which cyclotrimerize to form substituted triazine rings upon heating (or co-react with epoxies to form oxazoline linkages). Because no leaving groups or volatile byproducts are formed during co-cure of the cyanate ester monomer with epoxy, these curing reactions are referred to as addition polymerization. Suitable polycyanate ester monomers that may be used in the practice of the present invention include, for example:

1,1-bis(4-cyanatophenyl) methane;
1,1-bis(4-cyanatophenyl)ethane;
2,2-bis(4-cyanatophenyl)propane;
1,3-bis[2-(4-cyanatophenyl)propyl]benzene;
1,1-bis(4-cyanato-3,5-dimethylphenyl) methane;
1,1,1,3,3,3-hexafluoro-2,2-bis(4-cyanatophenyl) propane;
XU 71787™(Dow Chemical); and the like.

Cyanate ester monomers contemplated for use in accordance with the present invention may be readily prepared by reacting appropriate dihydric phenols with a cyanogen halide in the presence of an acid acceptor (See, for example, U.S. Pat. Nos. 3,994,949, 4,028,393 and 4,748,280, each of which is hereby incorporated by reference herein in its entirety).

In certain applications, it is highly desirable to use monomers that impart hydrophobicity to the cured thermoset polymer. This feature is particularly desirable when the cured polymer is required to withstand exposure to moisture, especially at elevated temperatures. Suitable commercially available cyanate ester monomers that would impart this property include RTX-366™, AROCY M-10™, and AROCY F-10™ (all from Ciba), XU 7178™, and the like, with RTX-366™ and XU 7178™ being the most hydrophobic, and therefore presently the most preferred.

Epoxy monomers (other than invention non-aromatic epoxies) that may be employed as co-reactants in the practice of the present invention are selected from those monomers that are sufficiently reactive to yield a desirable cure profile. Aromatic epoxy monomers tend to be preferable to aliphatic monomers, as aromatic monomers are typically more reactive. For example, glycidyl ether, glycidyl ester, and glycidyl amine-type epoxies typically work well in accordance with the present invention.

In one embodiment of the present invention, epoxy monomer co-reactant(s) contemplated for use in thermosetting resins have the structure:

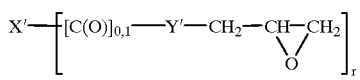

wherein:
X' is monovalent or polyvalent aliphatic, substituted aliphatic, aromatic, substituted aromatic, or polyether;
Y' is O or NQ, wherein Q is

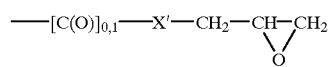

r'=1, 2, 3 or 4.

When used in reference to the X' moiety of the above-described epoxy monomer, "aliphatic" refers to a straight chain or branched chain hydrocarbon radical containing about 4 to about 40 carbon atoms in its molecular structure. "Substituted aliphatic" refers to a hydrocarbon radical further bearing one or more substituents such as hydroxy, alkoxy (of a lower alkyl group), mercapto (of a lower alkyl group), aryl, heterocyclic, halogen, trifluoromethyl, pentafluoroethyl, cyano, cyanomethyl, nitro, amino, carboxyl, sulfonyl, sulfonamide, and the like. "Aromatic" refers to any hydrocarbon radical, whether or not it contains atoms other than hydrogen and carbon, that has aromatic character as understood by those skilled in the art. "Substituted aromatic" refers to aromatic radicals further bearing one or more substituents as set forth above with respect to the substituted aliphatic moiety. "Polyether" refers to compounds of the structure:

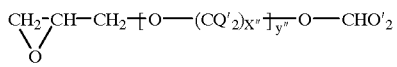

wherein:
x"=1–4;
y"=2–100; and
$Q^1$ H or lower alkyl.

Preferred epoxy monomers contemplated for use as co-reactants in the practice of the present invention include diglycidyl ether of bisphenol F (sold as, e.g., EPICLON-830LVPP™ (Dainippon Ink & Chemicals, Tokyo) and RSL-2007™), poly(propylene glycol) diglycidyl ether (PPGDGE), N,N,N',N'-tetraglycidyl-4,4'-diaminodiphenylmethane, triglycidyl tris(hydroxy phenyl) methane, glycidated phthalic acid, glycidated isophthalic acid, glycidated terephthalic acid, glycidated p-amino phenol, glycidated bisphenol E, glycidyl ether of bisphenol F, bisglycidyl ether of Bisphenol A, glycidated dimer acid, and the like. Also preferred are commercially available epoxy monomers such as HELOXY 71™ and HELOXY 505™(both from Shell), and the like. Both of these epoxy monomers impart flexibility to the cured thermoset as well as hydrophobicity. The presently most preferred epoxy monomers are polyfunctional epoxies such as epoxy novolac (e.g., ARATRONIC 5057™ (Cibia)) or epoxy cresol novolac (e.g., SUMI—EPOXY ESCN—195™ (Sumitomo)), and the like.

Anhydrides contemplated for use as co-reactants in the practice of the present invention include hexahydro-4-methylphthalic anhydride, hexahydro-phthalic anhydride, succinic anhydride, maleic anhydride, 3,3',4,4'-benzophenone tetracarboxylic dianhydride (BDTA), pyromellitic dianhydride (PMDA), 4,4'-oxydiphthalic anhydride (ODPA), 3,3',3,3'-biphenyl tetracarboxylic dianhydride (δ-BPDA), and the like. Other suitable anhydrides include siloxane-bridged anhydrides, such as those described in U.S. Pat. No. 4,381,396, incorporated by reference herein in its entirety.

Organic acids contemplated for use as co-reactants in the practice of the present invention include phthalic and terephthalic acids, and the like.

In accordance with one aspect of the present invention the curing agent is one or more of a Lewis acid, a metal catalyst, an imidazole, a tertiary amine, a cationic catalyst, and the like.

Lewis acids contemplated for use in the practice of the present invention have a metal component selected from B, Al, Pb, Fe, Co, Ni, Cu, Zn, Sn, Mn, or the like; and a solubilizing component such as a long chain fatty acid, a chelating ligand (e.g., AcAc), an amine complex, and the like.

Metal catalysts will typically only be employed when cyanates and epoxidized derivatives of glycidyl ether are employed. Suitable metal catalysts contemplated for use in the practice of the present invention are preferably transition metal acetylacetonates or other metal chelates and/or metal soaps. Examples of suitable metals contemplated for use herein include cobalt, manganese, tin, zinc, copper, nickel, and the like, all in the divalent state; manganese, iron, cobalt aluminum, and the like, all in the trivalent state; tetravalent titanium; metal soaps of all of the above; and the like. The presently most preferred metal catalyst is cobalt(III) acetylacetonate.

Imidazoles contemplated for use as catalysts for curing the epoxy monomers in the practice of the present invention include any imidazole that is effective for catalyzing the polymerization of an epoxy monomer. In one embodiment, the imidazole has the structure:

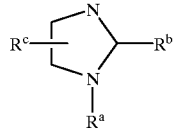

wherein $R^a$ is hydrogen, alkyl, aryl, or cyano; $R^b$ is hydrogen, alkyl, aryl, or cyano; and $R^c$ is hydrogen, alkyl, substituted alkyl, alkylaryl, or substituted alkylaryl. Suitable imidazoles include, for example, 2-ethyl-4-methyl imidazole (also referred to as CURIMIDE-24™), imidazole, 1-methyl imidazole, 2-methyl imidazole, 2-undecylimidazole, 2-phenyl imidazole, and the like, with CURIMIDE-24™ being the currently preferred imidazole. Preferably, the imidazole is present in a concentration of between about 0.5 and about 15 weight percent, relative to the amount of epoxy monomer(s) present in the composition. It is presently preferred that the imidazole concentration is between about 1.0 and about 10.0 weight percent, relative to the epoxy monomer(s).

Cationic catalysts contemplated for use in the practice of the present invention include onium salts, iodonium salts, sulfonium salts, and the like.

Fillers contemplated for use in the practice of the present invention may optionally be conductive (electrically and/or thermally). Electrically conductive fillers contemplated for use in the practice of the present invention include, for example, silver, nickel, gold, cobalt, copper, aluminum, graphite, silver-coated graphite, nickel-coated graphite fillers, alloys of such metals, and mixtures thereof, and the like. Both powder and flake forms of filler may be used in the attach paste compositions of the present invention. Preferably, the flake has a thickness of less than about 2 microns, with planar dimensions of about 20 to about 25 microns. Flake employed herein preferably has a surface area of about 0.15 to 5.0 $m^2$/g and a tap density of about 0.4 up to about 5.5 g/cc. It is presently preferred that powder employed in the practice of the present invention has a diameter of about 0.5 to 15 microns.

Thermally conductive fillers contemplated for use in the practice of the present invention include, for example, aluminum nitride, boron nitride, silicon carbide, diamond, graphite, beryllium oxide, magnesia, silica, alumina, and the like. Preferably, the particle size of these fillers will be about 20 μm. If aluminum nitride is used as a filler, it is preferred that it be passivated via an adherent, conformal coating (e.g., silica, or the like).

Electrically and/or thermally conductive fillers are optionally (and preferably) rendered substantially free of catalytically active metal ions by treatment with chelating agents, reducing agents, nonionic lubricating agents, or mixtures of such agents. Such treatment is described in U.S. Pat. No. 5,447,988, which is incorporated by reference herein in its entirety.

Optionally, a filler may be used that is neither an electrical nor thermal conductor. Such fillers may be desirable to impart some other property such as a reduced dielectric constant, improved toughness, increased hydrophobicity, and the like. Examples of such fillers include perfluorinated hydrocarbon polymers (i.e., TEFLON™), thermoplastic polymers, thermoplastic elastomers, mica, fused silica, and the like.

The invention will now be described in greater detail by reference to the following non-limiting examples.

EXAMPLE 1
COMPARISON OF INVENTION RESINS WITH COMMERCIALLY AVAILABLE RESINS

A comparison of three different epoxies is shown in Table 1. The "NQPR" resin represents a polycyclic epoxy generated via a Diels-Alder cycloaddition of 5-vinyl-norbornene and cyclopentadiene (as further detailed below), followed by epoxidation. The two NQPR lots shown both contained mostly five ring species (polycyclic rings are counted as one ring). The "QPR" resin was a material made by subjecting cyclopentadiene monomer to Diels-Alder cycloaddition reaction, followed by epoxidation with peracetic acid. The QPR resin contained approximately a 1:1 ratio of three ring species and four ring species. The "ECN" resin is a commercially available epoxy-cresol-novolac resin that has been used in the industry in epoxy mold compound formulations. The properties summarized in Table 1 show the relative epoxy equivalent weight (EEW), viscosity, and melting points for all of these materials. It is worth noting that both the NQPR and QPR resins are significantly lower in viscosity than the ECN. The higher EEW for the NQPR is also consistent with the higher average number of rings in this product.

TABLE 1

Epoxy Resin Characteristics

| Resin | EEW g/eq. | Cone & Plate Viscosity @ 125° C. (centipoise) | Ring & Ball Melt Point, ° C. |
|---|---|---|---|
| NQPR (lot #1) | 262 | 490 | 67.5 |
| NQPR (lot #2) | 257 | 560 | 65.5 |
| QPR | 188 | 130 | 80 |
| ECN | 196 | >1,000 | 65 |

The NQPR, QPR, and ECN resins were each mixed with 80% of the theoretical equivalent weight of 3,3',4,4'-benzophenone tetracarboxylic dianhydride (BTDA) and zinc octoate catalyst (typically about 2 wt %). Gel times at several temperatures were determined for these mixtures using differential scanning calorimetry (DSC). The results of these tests are shown in Table 2.

TABLE 2

DSC Reaction Times with BTDA @ 80% anhydride/epoxy equivalent (A/E) Stoichiometry (Zn-Octoate Catalyst)

| | Minutes to Gel | | | |
|---|---|---|---|---|
| Resin | 150° C. | 160° C. | 170° C. | 180° C. |
| QPR | 28 | 19 | 13 | 8.5 |
| QPR/ECN (50/50) | 9.1 | 5.7 | 3.5 | 2.1 |
| ECN | 6.5 | 3.9 | 2.3 | 1.4 |
| NQPR | 8.5 | 4.0 | 1.7 | 0.8 |

The QPR gave a slower cure than the other epoxy resins here, but a mix containing equal portions of QPR and ECN had a gel time much closer to that of the commercially available ECN resin. The NQPR resin had gel times that were equivalent to or better than the ECN material.

Mold compound formulations were made using the 50/50 blend of QPR and ECN with various anhydride/epoxy equivalent (A/E) ratios. These mixtures contained various levels of fused silica filler and were catalyzed either with zinc octoate (typically about 2 wt %) or benzyldimethylamine (BDMA) (typically about 2 wt %). The properties associated with these compositions are summarized in Table 3.

TABLE 3

QPR/ECN/BTDA Compounds

| Formulation Description/Data | A | | B | | C | |
|---|---|---|---|---|---|---|
| A/E, % | 61 | | 77 | | 69 | |
| Catalyst | Zn-Octoate | | BDMA | | BDMA | |
| % Spherical FS[1] | 72.8 | | 73.2 | | 78.0 | |
| Data @ 177° C. | | | | | | |
| Flow, inches | 58 | | 62 | | 58.5 | |
| Gel, seconds | 18 | | 39 | | 30 | |
| DSC ΔH, J/g | 55.1 | | 44.4 | | 41.5 | |
| Peak Exotherm, ° C. | 145 | | 176 | | 173 | |
| Act. Energy, KJ/mole | 93.3 | | 111.4 | | 118.0 | |
| | NPC[2] | PC[3] | NPC | PC | NPC | PC |
| Tg, ° C. | 159 | 215 | 149 | 213 | 160 | 192 |
| CTE[4],ppm/° C. @ Cure Temp. of | 16.1 | 16.1 | 10.3 | 14. | 7.6 | 11.8 |
| 50° C. | | | | | | |
| 80–100° C. | 17.6 | 16.4 | 10.4 | 14.6 | 13.3 | 13.9 |
| 220–240° C. | 0.73 | NA | 44.1 | 44.7 | 36.5 | 32.2 |
| Water Absorption 85° C./85% RH[5] | NPC | PC | NPC | PC | NPC | PC |
| 24 Hrs | 0.35 | 0.37 | 0.25 | 0.28 | 0.21 | 0.23 |
| 96 Hrs | 0.73 | 0.76 | 0.50 | 0.54 | 0.41 | 0.44 |
| 168 Hrs | 0.73 | 1.00 | 0.67 | 0.70 | 0.55 | 0.57 |

[1]FS = Fused silica
[2]NPC = No Post cure
[3]PC = Post cure 4 Hrs @ 175° C.
[4]CTE = Coefficient of Thermal Expansion
[5]RH = Relative Humidity The zinc octoate was shown to be a more active catalyst than BDMA. The glass transition temperatures were outstanding for all of the compositions, particularly following post mold cure. High filler loadings were possible since the resin viscosity was so low. This, in turn, allowed these compositions to attain very low coefficients of thermal expansion. Moisture uptake was also very low for all of these compositions.

Formulation C was then compared to "MG15F" which is a commercial, anhydride cured, ECN-resin-based mold compound. (Formulation C was chosen because its fused silica content reduces flammability and cost while retaining desirable rheologic properties). Table 4 summarizes the composition and properties of these two mold compound formulations. Post cure conditions are the same as above.

TABLE 4

QPR/ECN/BTDA Compound Comparison to Standard Mold Compound

| Formulation Description/Data | MGI5F (Reference Compound) | C |
|---|---|---|
| A/E, % | 78 | 69 |
| Catalyst | IM0391 | BDMA |
| % Filler | 69 | 78 |
| Data @ 177° C. | | |
| Flow, inches | 22.5 | 58.5 |
| Gel, seconds | 22 | 30 |
| Specific Gravity | 1.80 | 1.88 |
| DSC | 37.2 | 41.5 |

TABLE 4-continued

QPR/ECN/BTDA Compound Comparison to Standard Mold Compound

| Formulation Description/Data | MG15F (Reference Compound) | | | C |
|---|---|---|---|---|
| ΔH,J/g |  |  |  |  |
| Peak Exotherm, ° C. | 168.5 | | | 173 |
| Act. Energy, KJ/mole | 130.7 | | | 118.0 |
|  | NPC | PC | NPC | PC |
| Tg, ° C. | 146 | 168 | 159 | 192 |
| CTE, ppm/° C. | 0.73 | 21.1 | 7.6 | 11.8 |
| @ Cure Temp. of |  |  |  |  |
| 50° C. |  |  |  |  |
| 80–100° C. | 24.1 | 24.9 | 13.3 | 13.9 |
| 220–240° C. | 59.7 | 61.2 | 36.5 | 32.2 |

The MG15F had much lower flow than Invention Formulation C even though it had much lower filler content. The gel times were fairly comparable while the Tg and CTE values were clearly superior for the Invention Formulation C.

Dielectric analysis (DEA) was also performed on MG15F and Invention Formulation C. Measurements were made for "as molded" and "post mold cured" samples. The "as molded" results are summarized in Table 5 while the "post mold cured" results are shown in Table 6.

In order to demonstrate the superior hydrolysis resistance and hydrophobicity of invention epoxies as compared to commercially available epoxy resins, invention formulation QPR (as described in Example 1) was compared to ERL-4221 (Union Carbide).

QPR and ERL-422 1 were each cured by mixing with hexahydro-4-methylphthalic anhydride (HHMPA) at 0.55 equivalents per equivalent of epoxy, stannous octoate at 0.5 parts per hundred epoxide resin, and 1% by weight of propylene glycol. The mixture was stirred until homogenous (in the case of the QPR formulation, the mixture was heated gently). Each mixture was then degassed in a vacuum chamber for approximately 30 minutes and then poured into a TEFLON™ coated mold. The mixtures were again subject to vacuum to ensure that bubbles do not form in the cured strips of resin. Each mixture was then heated as follows:

ERL-4221 resin: 2 hrs at 100° C. followed by 4 hrs at 160° C.;

QPR resin: 2 hrs at 175° C. followed by 2 hrs at 250° C.

The initial weight of three samples was recorded and then the samples were tested for moisture retention and susceptibility to hydrolysis by autoclaving at a temperature of 121° C. at 2 atm of pressure. Samples were periodically removed and weighed. The change in weight was recorded and the results were plotted in a graph (FIG. 1).

As illustrated in FIG. 1, the commercially available resin was both hydrophilic and susceptible to hydrolysis as evidenced by a pattern of gaining moisture (increasing weight),

TABLE 5

Non-Postcured Dielectric Analysis Data @ 0.3 Hz

| Formulation | Ionic Conductivity pmho/cm | | Permittivity | | Loss Factor | | Dissipation Factor | |
|---|---|---|---|---|---|---|---|---|
|  | 50° C. | 200° C. | 50° C. | 200° C. | 50° C. | 200° C. | 50° C. | 200° C. |
| C | 0.0004 | 0.0688 | 3.36 | 3.90 | 0.0024 | 0.4124 | 0.0007 | 0.1054 |
| MG15F | 0.0051 | 0.2467 | 3.61 | 4.55 | 0.0307 | 1.48 | 0.0085 | 0.3227 |

TABLE 6

Postcured Dielectric Analysis Data @ 0.3 Hz

| Formulation | Ionic Conductivity pmho/cm | | Permittivity | | Loss Factor | | Dissipation Factor | |
|---|---|---|---|---|---|---|---|---|
|  | 50° C. | 200° C. | 50° C. | 200° C. | 50° C. | 200° C. | 50° C. | 200° C. |
| C | 0.0003 | 0.0595 | 3.37 | 3.74 | 0.0021 | 0.3564 | 0.0006 | 0.0949 |
| MG15F | 0.0044 | 0.2909 | 3.60 | 4.66 | 0.0263 | 1.74 | 0.0073 | 0.3692 |

The DEA ionic conductivity, permittivity, loss factor, and dissipation factor values were all remarkably better for Invention Formulation C than MG15F. The ionic conductivity, loss factor and dissipation factor, in particular, were all more than one order of magnitude lower at 50° C. for the Invention Formulations than they were for the control mold compound. The DEA performance is considered to be a useful predictor for in service performance (especially for hot and humid environments) of a mold compound. The values measured for Invention Formulation C indicates that this material has superior performance characteristics.

EXAMPLE 2
COMPARISON OF AN INVENTION FORMULATION TO A COMMERCIALLY AVAILABLE RESIN:

followed by hydrolysis (losing weight). In contrast, the invention formulation exhibited much greater stability, gaining only 3 to 4% of its initial weight and exhibiting no weight loss due to hydrolysis.

EXAMPLE 3
PREPARATION OF CYCLOPENTADIENE OLIGOMER:

The cyclopentadiene oligomer was prepared in a one liter two neck flask, equipped with a magnetic stirring bar, a Teflon coated thermocouple (attached to a temperature controller), and a reflux condenser. In a typical procedure 500 g of dicyclopentadiene (DCPD) from Aldrich was melted and added to the flask, the temperature of the liquid was raised to about 155–175° C., and allowed to reflux for approximately eighteen to twenty hours. The initial reflux started at about 155° C., and then over time the temperature was raised slowly to continue the reflux. However, if the temperature rises above 180° C. for a significant amount of time the material will start to solidify. This solid material (which is believed to be high molecular weight polycyclics) was not of much use due to the fact that it is insoluble in organic solvents, and thereforee did not readily undergo subsequent synthetic transformations.

After the eighteen to twenty hours at temperature, the mixture was placed on a Kugelrohr ball-tube distillation aparatus, and at full vacuum (approximately 0.5 Torr) all of the unreacted DCPD, and low molecular weight components were stripped off at an air bath temperature of up to 100° C. After cooling, the remaining contents in the flask solidified into a waxy solid. Based on the $^1$H NMR integration of this material it is estimated that there remains a $C_{15}$–$C_{20}$ mixture (3–4 rings). This material was then set aside for epoxidation.

EXAMPLE 4
EPOXIDATION OF CYCLOPENTADIENE OLIGOMER:

A five liter flask equipped with mechanical stirring, pressure equalized dropping funnel, and a cold water bath, was used in a typical procedure. Into this flask was placed 242 g (1.052 mole) of the trimer, tetramer mixture of cyclopentadiene obtained as described in Example 3. The waxy material was dissolved in approximately three liters of methylene chloride. Next, 224 g (~2.1 mole) of sodium carbonate was added to the flask. To the dropping funnel was added 550 g (2.52 mole, about a twenty percent excess) of thirty-five percent peracetic acid solution in acetic acid. This peracetic acid solution contains about one percent sulfuric acid, which was neutralized with seven grams of sodium acetate. The mixture in the flask was stirred vigorously at 0 to 10° C., while the peracetic acid solution was added dropwise over one hour. The addition rate and temperature of the reaction should be monitored, because a great deal of carbon dioxide was generated in the reaction mixture. The reaction was typically allowed to stir overnight (12–16 hrs.) for completion. The next day the solution was placed in a large separatory funnel, and was washed with 3×500 mL of saturated sodium bicarbonate solution to remove any remaining acetic acid. Drying the solution over magnesium sulfate followed a final wash with saturated sodium chloride solution. The solvent was then removed using a rotary evaporator to obtain a white solid. Mechanical vacuum was used as a last step to remove all traces of solvent. The final product ~250 g obtained was a white waxy solid (~90% yield). The final product was analyzed by $^1$H NMR spectroscopy, and it was determined that the epoxidation was >95% complete, marked by the disappearance of olefinic protons.

EXAMPLE 5
PREPARATION OF DICYCLOPENTADIENE-VINYLNORBORNENE OLIGOMER

Vinylnorbornene is a Diels-Alder product of cyclopentadiene and butadiene, which boils at 141 ° C. at atmospheric pressure. Since its boiling point is too low to conduct the desired Diels-Alder cyclopentadiene additions and also to prevent loss of butadiene (i.e. via any retro Diels-Alder reaction) this oligomer was made using a Parr reactor. In a typical procedure 443 g (~3.69 mole) of vinylnorbornene was placed in he Parr reactor, followed by 162 g (~1.23 mole) of dicyclopentadiene. Subsequently, the reactor was sealed and the mixture was heated to 220° C. During the heating process the pressure in the reactor increased to ~100 psi, and after several hours it dropped to about thirty psi.

After four hours at temperature, the heat was turned off and the reactor was allowed to cool down to room temperature (requiring several hours). After the reactor was cool enough to open, an additional 132 g (one mole) of dicyclopentadiene was added to the Parr reactor, and the heating was resumed at 220° C. for an additional fifteen to sixteen hours. After the reaction contents were heated for the desired length of time, heating was discontinued and the vessel was allowed to cool. When the vessel had cooled sufficiently, the liquid was transferred to a round bottom flask and all of the volatiles were stripped off using a Kugelrohr ball-tube distillation apparatus, at an air bath temperature of 150° C. at full vacuum. The material remaining in the flask gelled upon cooling. Typically about 50% of the original starting material remains. Based on the $^1$H NMR of the collected material the end groups are deduced to be vinyl, norbornenyl, or cyclohexenyl. Based on the fact that it does not solidify, the molecules apparently have a degree of rotational freedom. The average molecular weight of this mixture was determined to be about 300 g/mole by $^1$H NMR integration.

EXAMPLE 6

EPOXIDATION OF DICYCLOPENTADIENE-VINYLNORBORNENE OLIGOMER

Epoxidation of dicyclopentadiene-vinylnorbornene oligomer from the preceding Example was carried out according to the general procedure described in Example 4, using peracetic acid in methylene chloride. In this case an ~85% yield of glassy solid was obtained. This solid can be crushed to a fine powder. The $^1$H MR again shows that the epoxidation is >95% complete, marked by the disappearance of the olefinic protons.

EXAMPLE 7

PREPARATION OF NORBORNENYL GLYCIDYL ETHER

A one-liter round bottom flask was equipped with a stirring bar, claisen head, pressure equalized dropping funnel, and condenser. To this flask was added 171 g (~1.5 mole) of allyl glycidyl ether, the liquid was brought to reflux (~154° C.) using a heating mantle. In the dropping funnel was added 114 g (1 mole) of allyl glycidyl ether along with 132 g (1 mole) of dicyclopentadiene. Over the course of 6–8 hours this solution was added dropwise to the refluxing allyl glycidyl ether. After the addition was complete the solution was allowed to reflux overnight (12–16 hours). The contents of the reaction flask were then subjected to rotary evaporation and the excess allyl glycidyl ether was removed under reduced pressure in a 90° C. water bath. The other components were separated using a rotary evaporator at full vacuum. At 100–120° C., ~250 g of clear low viscosity liquid were collected, followed by 110 g of a more viscous second fraction collected at 150–170° C. A waxy solid remained in the reaction vessel after the distillation was concluded. Based on the $^1$H NMR integration, and thermogravimetric analysis, the first fraction was determined to be mononorbornenyl glycidyl ether (compound A), and the second fraction was determined to be dinorbornenyl glycidyl ether (compound B). The reaction vessel residue comprised higher molecular weight components.

(A)
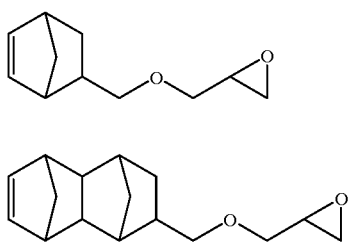

(B)
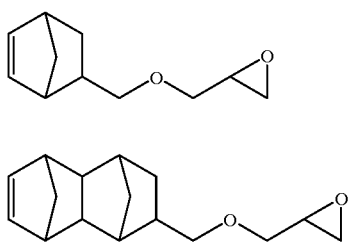

(D)
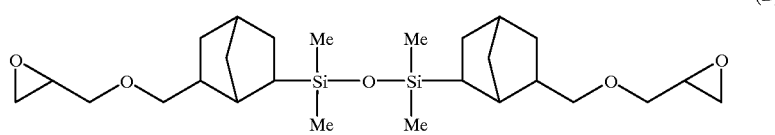

EXAMPLE 8
EPOXIDATION OF NORBORNENYL GLYCIDYL ETHER

Epoxidation of compound (A) from the preceding Example was carried out using the general procedure described in Example 4. An approximately 90% yield of a clear, low viscosity liquid, was obtained. Based on the $^1$H NMR it was determined that the epoxidation was >95% complete. The IR showed only a very small peak at ~1730 cm$^{-1}$. The near absence of any acetate ester shows that the glycidyl ether functionality is able to withstand the epoxidation procedure. This compound is unique in that it has two very different epoxy functionalities with different reactivities in the same molecule (compound C).

(C)
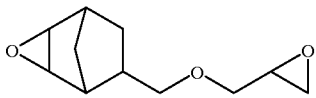

This compound is of interest because the different reactivities of the functional groups allow for stepwise polymerization or modification of the compound.

EXAMPLE 9
PREPARATION OF TETRAMETHYLDISILOXANE COUPLED NORBORNYL GLYCIDYL ETHER

A one-liter round bottom flask was equipped with a stirring bar and condenser. To this flask was added 317 g (1.76 mol) of norbomyl glycidyl ether (Compound A, Example 7), followed by 110 g (0.82 mol) of tetramethyldisiloxane. The flask was placed in an oil bath at an initial temperature of approximately 7°° C., and while stirring under a blanket of nitrogen, 2–3 drops of a 2% xylene solution of platinum(0)-1,3-divinyl-1,1,3,3-tetramethyldisiloxane complex (Karsted's catalyst) was quickly added. After stirring for 2–3 hrs, the temperature of the oil bath was raised to approximately 90–100° C., followed by continued stirring for a total of about 24 hrs to ensure complete hydrosilation. The completion of the reaction was evidenced by the disappearance of the silicon-hydrogen bond from the IR spectrum.

Following completion of the reaction, volatiles were stripped off under full vacuum using a Kugelrohr ball-tube distillation apparatus. The final product was a slightly yellow, low viscosity liquid of compound D.

This compound is of interest because it has low viscosity, two highly reactive epoxy groups and a hydrophobic backbone.

While the invention has been described in detail with reference to certain preferred embodiments thereof, it will be understood that modifications and variations are within the spirit and scope of that which is described and claimed.

What is claimed is:

1. A cycloaliphatic epoxy monomer having the following structure:

(X)
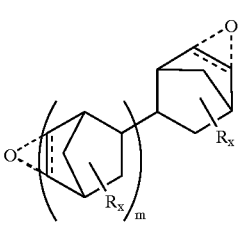

wherein each R is independently lower alkyl or halogen, m is 1 up to about 9, and each x is independently 0, 1, or 2.

2. A cycloaliphatic epoxy monomer according to claim 1, wherein m is 1 up to about 5.

3. A thermosetting resin composition comprising:
   (a) a cycloaliphatic epoxy monomer according to claim 1,
   (b) a curing agent,
   (c) optionally, a co-reactant, and
   (d) optionally, a filler.

4. A thermosetting resin according to claim 3, wherein said curing agent is one or more of a Lewis acid, a metal catalyst, an imidazole, or a cationic catalyst.

5. A thermosetting resin according to claim 3, wherein said co-reactant, if present, has the ability to promote ring opening of epoxides.

6. A thermosetting resin according to claim 3, wherein said co-reactant is one or more of an epoxy, a cyanate ester, an anhydride, an organic acid, a polyamine, a polyamide, a polysulfide, or a polyhydroxy hydrocarbyl.

7. A thermosetting resin according to claim 6, wherein said anhydride is hexahydro-4-methylphthalic anhydride, hexahydro-phthalic anhydride, succinic anhydride, maleic anhydride.

8. A thermosetting resin according to claim 4, wherein said Lewis acid has a metal component selected from Al, B, Pb, Fe, Co, Ni, Cu, Zn, Sn, or Mn.

9. A thermosetting resin according to claim 4, wherein said Lewis acid has a solubilizing component comprising a long chain fatty acid, a chelating ligand or a tertiary amine.

10. A thermosetting resin according to claim 3, wherein said filler, if present, is conductive.

11. A thermosetting resin according to claim 3, wherein said filler, if present, is electrically conductive and/or thermally conductive.

12. A thermosetting resin composition according to claim 3, wherein said filler, if present, is non-conductive.

13. A thermosetting resin composition according to claim 12, wherein said filler is a perfluorinated hydrocarbon.

* * * * *

UNITED STATES PATENT AND TRADEMARK OFFICE
CERTIFICATE OF CORRECTION

PATENT NO. : 6,429,281 B1
DATED : August 6, 2002
INVENTOR(S) : Dershem et al.

It is certified that error appears in the above-identified patent and that said Letters Patent is hereby corrected as shown below:

Column 14,
Line 6, delete "ERL-422 1" and substitute --ERL-4221--

Column 16,
Line 34, delete "MR" and substitute -- NMR --

Column 17,
Line 58, delete "$7^{0o}$" and substitute -- 70° --

Signed and Sealed this

Eleventh Day of February, 2003

JAMES E. ROGAN
*Director of the United States Patent and Trademark Office*